US012109037B2

(12) United States Patent
Lee

(10) Patent No.: US 12,109,037 B2
(45) Date of Patent: Oct. 8, 2024

(54) APPARATUS AND METHOD FOR PRECISE ANALYSIS OF SEVERITY OF ARTHRITIS

(71) Applicant: CRESCOM Co., Ltd., Seongnam-si (KR)

(72) Inventor: Jae Joon Lee, Yongin-si (KR)

(73) Assignee: CRESCOM CO., LTD., Seongnam-si (KR)

(*) Notice: Subject to any disclaimer, the term of this patent is extended or adjusted under 35 U.S.C. 154(b) by 395 days.

(21) Appl. No.: 17/616,747

(22) PCT Filed: Jul. 16, 2020

(86) PCT No.: PCT/KR2020/009402
§ 371 (c)(1),
(2) Date: Dec. 6, 2021

(87) PCT Pub. No.: WO2021/010777
PCT Pub. Date: Jan. 21, 2021

(65) Prior Publication Data
US 2022/0330887 A1 Oct. 20, 2022

(30) Foreign Application Priority Data
Jul. 17, 2019 (KR) .................. 10-2019-0086641

(51) Int. Cl.
*A61B 5/00* (2006.01)
*A61B 6/00* (2006.01)
(Continued)

(52) U.S. Cl.
CPC .............. *A61B 5/4528* (2013.01); *A61B 6/00* (2013.01); *G06T 7/00* (2013.01); *G16H 30/40* (2018.01); *G16H 50/20* (2018.01)

(58) Field of Classification Search
CPC ....... A61B 5/4528; A61B 6/00; A61B 5/0033; A61B 5/4509; A61B 5/7267;
(Continued)

(56) References Cited

U.S. PATENT DOCUMENTS

2011/0055141 A1* 3/2011 Jamil ..................... G06N 20/00
706/54
2013/0137962 A1* 5/2013 Urish .................. A61B 5/7264
600/410
(Continued)

FOREIGN PATENT DOCUMENTS

| JP | 2004-057804 | 2/2004 |
|---|---|---|
| KR | 10-2019-0023003 | 3/2019 |
| KR | 10-2019-0030151 | 3/2019 |

OTHER PUBLICATIONS

Ho-Chul Kang et al., "A Study of Joint Space Narrowing and Erosion in Rheumatoid Arthritis", Journal of Korean Society of Medical Informatics 15-4, 483-492, Dec. 2009.
(Continued)

*Primary Examiner* — Dhaval V Patel
(74) *Attorney, Agent, or Firm* — LEX IP MEISTER, PLLC

(57) ABSTRACT

An apparatus for a precise analysis of a severity of arthritis includes an image collection unit configured to collect a medical image having captured a joint of a user, a region detection unit configured to detect one or more regions of interest for analyzing arthritis in the medical image through a learned automatic region detection model, an individual analysis unit configured to extract quantitative feature values from the detected regions of interest and derives one or more individual analysis data from among a severity of arthritis, a severity of osteoproliferation, and a severity of hardness of a subchondral bone based on the feature values, and an integrated analysis unit configured to finely classify a sever-
(Continued)

ity of degenerative arthritis through an integrated analysis model learned based on the individual analysis data.

11 Claims, 7 Drawing Sheets

(51) Int. Cl.
    *G06T 7/00*            (2017.01)
    *G16H 30/40*         (2018.01)
    *G16H 50/20*         (2018.01)

(58) Field of Classification Search
    CPC . A61B 5/7275; A61B 5/7485; A61B 2576/00; A61B 6/5217; G06T 7/00; G06T 2207/10081; G06T 2207/10088; G06T 2207/10104; G06T 2207/20081; G06T 7/0012; G06T 2207/10116; G06T 2207/10132; G06T 2207/20084; G06T 2207/30008; G16H 30/40; G16H 50/20; G16H 50/70

See application file for complete search history.

(56) References Cited

U.S. PATENT DOCUMENTS

| | | | |
|---|---|---|---|
| 2013/0338496 A1* | 12/2013 | Hielscher | A61B 5/0064 |
| | | | 600/425 |
| 2016/0213278 A1 | 7/2016 | Urish et al. | |
| 2016/0321416 A1* | 11/2016 | Apte | G16H 40/67 |
| 2017/0202520 A1* | 7/2017 | Urish | A61B 5/055 |
| 2020/0405148 A1* | 12/2020 | Tran | A61B 3/0016 |
| 2021/0343389 A1* | 11/2021 | Cotty-Eslous | A61B 5/021 |

OTHER PUBLICATIONS

KIPO, Search Report & Written Opinion of Application No. PCT/KR2020/009402, Oct. 20, 2020.

* cited by examiner

APPARATUS AND METHOD FOR PRECISE ANALYSIS OF SEVERITY OF ARTHRITIS

TECHNICAL FIELD

An apparatus and method for a precise analysis of a severity of arthritis are provided.

BACKGROUND ART

Degenerative arthritis (osteoarthritis) is a disease in which inflammation and pain occur by breakdown of bones and ligaments constituting a joint, which results from damage or degeneration in cartilages that protects the joint.

Since such degenerative arthritis is caused by degeneration in joint cartilages, it is very important to relieve the pain, maintain a joint function, and prevent deformation through an accurate diagnosis at an early stage. If the deformation has already occurred, surgical correction and rehabilitation treatment must be performed, which results in a large economic cost and psychological adverse effects on a patient. In addition, the accurate diagnosis is important because the treatment such as appropriate drug therapy or artificial joint replacement is performed according to a progressing degree of the degenerative arthritis.

However, in a general diagnosis of the degenerative arthritis, the accuracy is often influenced by the experience or skill of medical staff.

Since reading of simple radiographic images, which is an initial diagnostic tool for the degenerative arthritis, is performed by each medical staff, the diagnosis and classification of abnormalities are applied differently due to differences in the readings for each medical staff, resulting in inappropriate treatment and loss of health insurance.

In order to improve the subjective reading of medical images, a method of learning and inferring a process of reading radiographic images using artificial intelligence is being studied recently.

However, in the diagnosis using the artificial intelligence, it is difficult to present a clear rationale for the abnormality classification of arthritis, and there may be deviations among learning models for medical images located at the boundary of grades.

Therefore, there is a need for a technique for quantifying the severity of arthritis and performing the diagnosis classification of arthritis to automatically classify and evaluate the disease.

DISCLOSURE

Technical Problem

An issue to be addressed by the present invention is to provide an apparatus and method for securing a basis for determining a severity of arthritis by analyzing features of each region based on artificial intelligence, and for accurately quantifying the severity of arthritis.

In addition to the above-described issue, the present invention may be used to address other issues not specifically mentioned.

Technical Solution

An apparatus for a precise analysis of a severity of arthritis according to an embodiment of the present invention includes an image collection unit configured to collect a medical image having captured a joint of a user, a region detection unit configured to detect one or more regions of interest for analyzing arthritis in the medical image through a learned automatic region detection model, an individual analysis unit configured to extract quantitative feature values from the detected regions of interest and derives one or more individual analysis data from among a severity of arthritis, a severity of osteoproliferation, and a severity of hardness of a subchondral bone based on the feature values, and an integrated analysis unit configured to finely classify a severity of degenerative arthritis through an integrated analysis model learned based on the individual analysis data.

The apparatus may further include a learning unit configured to detect regions of interest from a training medical image based on training data in which training medical images having captured a joint are matched with result data of reading the training medical images, and learns an individual analysis model configured to analyze a correlation between feature values extracted from the detected regions of interest and the result data.

The individual analysis model may include an arthritis severity analysis model configured to extract quantitative feature values for estimating reduction of a joint cavity based on a region of interest in which a joint cavity region is detected, an osteoproliferation severity analysis model configured to extract quantitative feature values for presence or absence of osteoproliferation or a progressing degree of osteoproliferation based on a region of interest in which an osteoproliferation probable region is detected, and a subchondral bone hardness severity analysis model configured to extract quantitative feature values for a progressing degree of subchondral bone hardness based on a region of interest in which a subchondral bone region is detected.

The individual analysis unit may estimate a medial value of the joint cavity and a lateral value of the joint cavity in the region of interest through the arthritis severity analysis model to extract a quantitative value of a severity of arthritis by an average of the medial value and the lateral value, and calculate a ratio of imbalance between the medial value and the lateral value.

The individual analysis unit may detect osteophyte or bone protrusion indicating osteoproliferation in the region of interest through the osteoproliferation severity analysis model, extract a corresponding osteoproliferation grade from among preset osteoproliferation grades, detect a degree of subchondral bone hardness in the region of interest through the subchondral bone hardness severity analysis model, and extract a corresponding hardness severity grade from among preset hardness severity grades of subchondral bone.

The learning unit may convert the individual analysis data obtained from the individual analysis model based on the training data into vectors, respectively, and learn the integrated analysis model configured to analyze a correlation between the vectors using the vectors. The integrated analysis model may include a degenerative arthritis severity analysis model configured to finely classify a severity for progressing degree of degenerative arthritis based on the individual analysis data, and a degenerative arthritis progression prediction model configured to predict progression of degenerative arthritis based on the individual analysis data and the severity of degenerative arthritis.

The integrated analysis unit may integrate the individual analysis data through the degenerative arthritis severity analysis model to precisely analyze the severity of degenerative arthritis in the medical image, and predict the progression of degenerative arthritis in future through the degenerative arthritis progression prediction model.

The apparatus may further include a control unit configured to output one or more feature values from among feature values corresponding to one or more individual analysis data derived from the individual analysis unit and features values for the severity of degenerative arthritis derived from the integrated analysis unit.

A program configured to be stored in a computer-readable storage medium and to be executed by a processor according to an embodiment of the present invention includes instructions to execute detecting, based on a collected medical image, one or more regions of interest for analyzing arthritis in the medical image through a learned automatic region detection model, extracting quantitative feature values from the detected regions of interest, deriving one or more individual analysis data from among a severity of arthritis, a severity of osteoproliferation, and a severity of subchondral bone hardness based on the feature values, finely classifying a severity of degenerative arthritis analyzed based on the individual analysis data, and outputting the classified severity of degenerative arthritis and the individual analysis data to a connected terminal.

Advantageous Effects

According to an embodiment of the present invention, it is possible to secure key feature values quantified in a detailed medical specialization field by acquiring individual analysis data from a region of interest detected from a medical image through an artificial intelligence model.

According to an embodiment of the present invention, it is possible to precisely classify and evaluate a severity of arthritis based on respective feature values of individual analysis data.

According to an embodiment of the present invention, it is possible secure a reliability of result data of the classified severity of arthritis by providing the individual analysis data that serves as a medical basis for classifying the severity of arthritis.

MODE FOR INVENTION

Figure 1A:
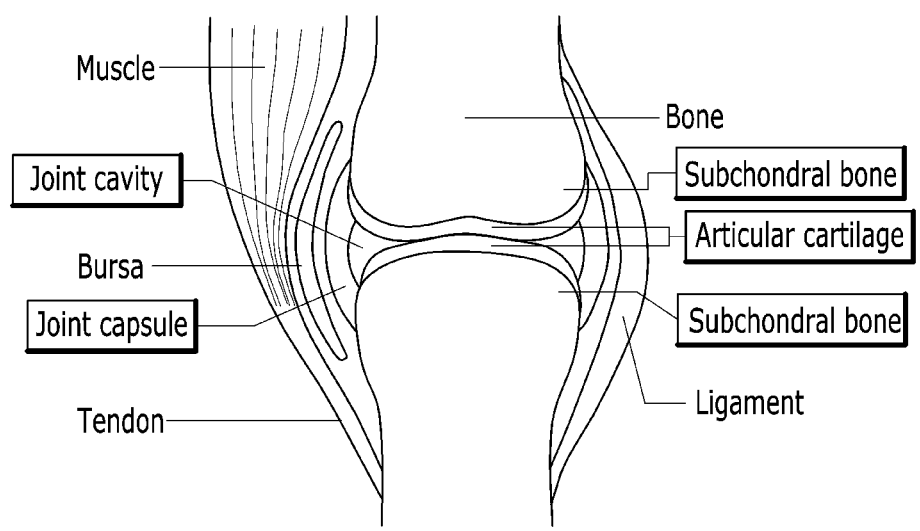
FIG. 1A and FIG. 1B are example drawings showing a structure of a joint and progression of arthritis.

In the following detailed description, only certain example embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification. In addition, in a case of a well-known known technology, a detailed description thereof is omitted.

When a part is referred to "include" or "comprise" a certain element, it means that it may further include other elements rather than exclude other elements, unless specifically indicates otherwise.

Figure 1B:
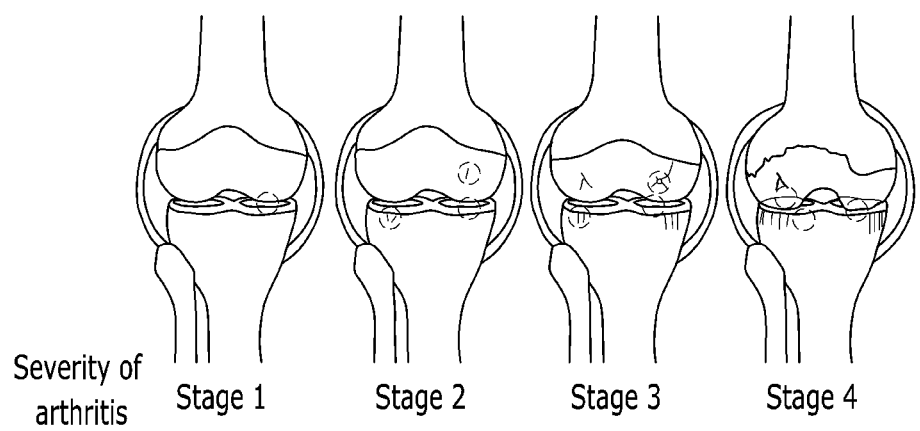

FIG. 1A and FIG. 1B are an example drawing showing a structure of a joint and progression of arthritis.

As shown in FIG. 1A, a joint is a connection made between two opposing bones and links the bones in a movable structure.

Each of the two bones has articular cartilage so that the two bones can move, and a joint capsule exists in an area surrounding the articular cartilage. A joint cavity exists inside the joint capsule, and a subchondral bone exists between the joint capsule and the bone. The joint cavity is a space between the two bones forming the joint and means a space (lumen) enclosed by synovial membrane (articular capsule). The subchondral bone means a part of the bone just below the cartilage.

FIG. 1B shows stages 1 to 4 according to a severity of arthritis.

Stage 1 represents a state in which a joint space is narrowed due to partial reduction of the cartilage and a joint disease begins. Stage 2 represents a state in which the narrow joint space and cartilage are damaged and hardness of subchondral bone ("subchondral bone hardness") begins. Stage 3 represents a state in which the joint space became narrower than in stage 2, a gap is enlarged due to the cartilage damage, and the subchondral bone hardness is in progress. Stage 4 represents a state in which the cartilage is reduced by less than half, the subchondral bone is deeply hardened, and the cartilage damage is exacerbated.

As shown in FIG. 1B, since the arthritis progresses simultaneously in multiple regions forming the joint, a progressing degree of each region and the overall joint condition are comprehensively analyzed to obtain a severity of arthritis, and a treatment method according to the severity of arthritis is chosen.

Figure 2:
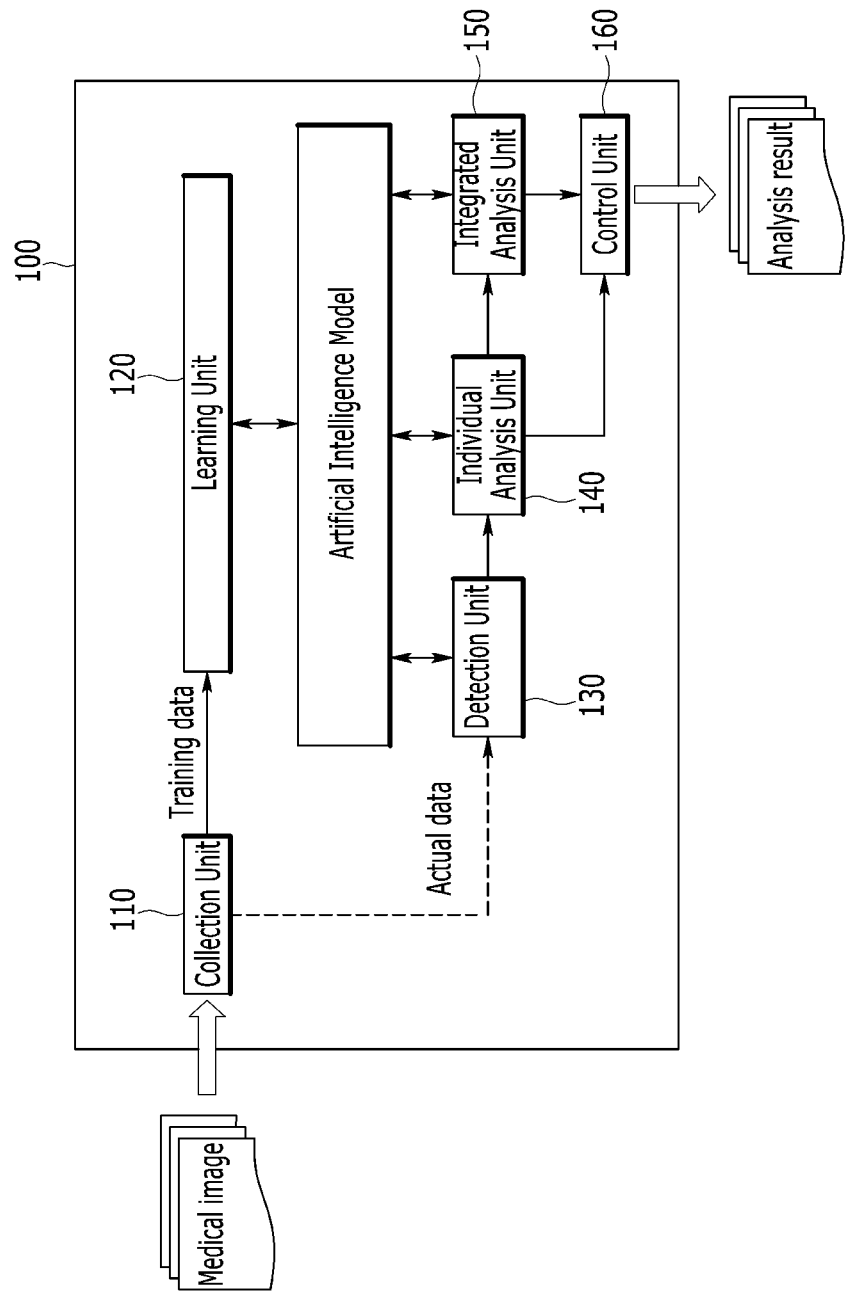
FIG. 2 is a structural diagram showing an apparatus for a precise analysis of a severity of arthritis according to an embodiment of the present invention.
Figure 3:
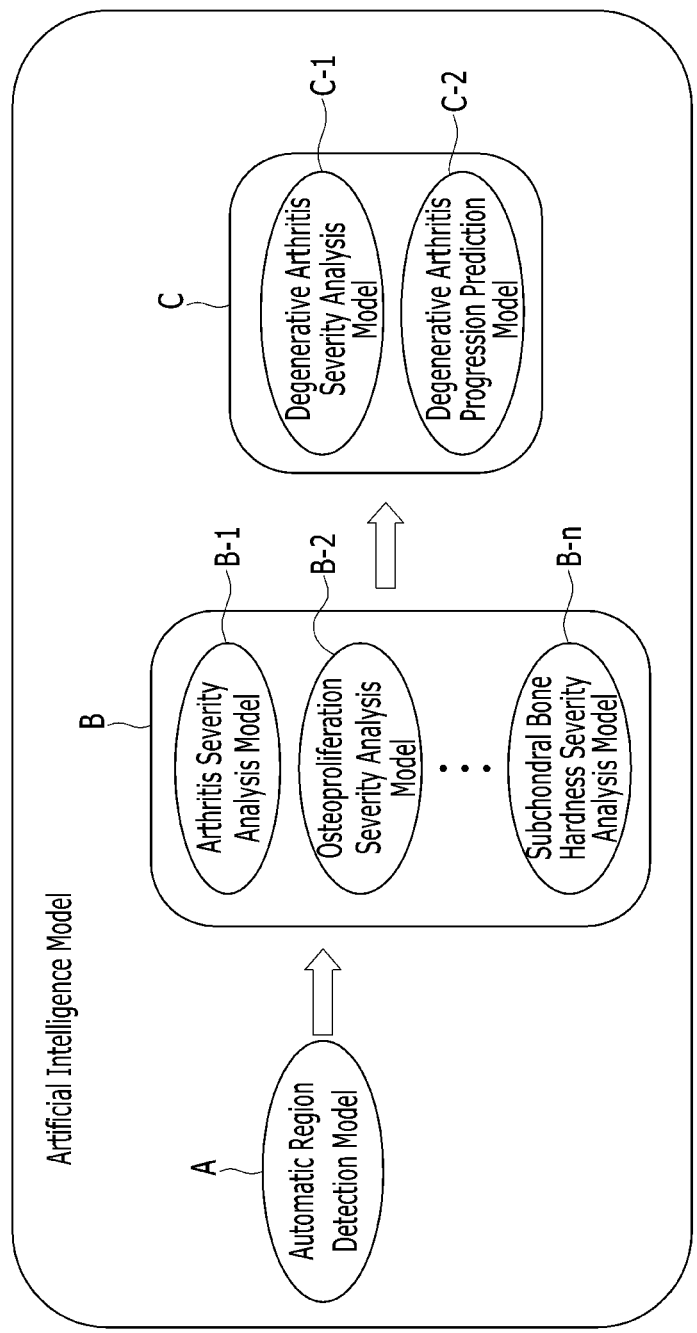
FIG. 3 is a schematic diagram showing an artificial intelligence algorithm according to an embodiment of the present invention.

FIG. 2 is a structural diagram showing an apparatus for a precise analysis of a severity of arthritis according to an embodiment of the present invention, and FIG. 3 is a schematic diagram showing an artificial intelligence algorithm according to an embodiment of the present invention.

As shown in FIG. 2, an apparatus 100 for precise analysis of a severity of arthritis collects a medical image and provides an analysis result obtained by performing individual analysis or integrated analysis on the medical image.

The apparatus 100 includes a collection unit 110, a learning unit 120, a detection unit 130, an individual analysis unit 140, an integrated analysis unit 150, and a control unit 160.

Although the collection unit 110, the learning unit 120, the detection unit 130, the individual analysis unit 140, the integrated analysis unit 150, and the control unit 160 are named for description, they are a computing device operated by one or more processors. Here, the collection unit 110, the learning unit 120, the detection unit 130, the individual analysis unit 140, the integrated analysis unit 150, and the control unit 160 may be implemented in one computing device, or may be distributed and implemented on different computing devices. When distributed on the different computing devices, the collection unit 110, the learning unit 120, the detection unit 130, the individual analysis unit 140, the integrated analysis unit 150, and the control unit 160 may communicate with each other through communication interfaces. A computing device is a device capable of executing a software program written to carry out the present invention.

The collection unit 110 collects medical images captured in real time from a connected medical image capturing device or collects medical images captured at a previous time from a connected database. The medical image refers to X-ray (or radiography) having captured a joint area, but is not limited thereto. The medical image may be a medical image among CT (computed tomography), PET (positron emission tomography), Ultrasound, MRI (magnetic resonance imaging), or the like.

Further, the collection unit 110 may collect medical images read by a plurality of image reading specialists and reading results of the medical images as training data. Here, in the training data, each medical image may be labeled with a reading result.

Furthermore, the collection unit 110 may pre-process the medical images based on an input format of an artificial intelligence model so that the collected medical images can be input to the artificial intelligence model. The pre-processing of medical images is a stage of increasing effects of artificial intelligence learning and analysis, and includes processes such as image quality improvement and equalization. For example, an accuracy of image analysis may be improved by applying contrast limited adaptive histogram equalization (CLAHE) or histogram equalization as a method of the image quality improvement.

The learning unit 120 learns the artificial intelligence model to detect a region of interest or derive analysis data in response to an input image by using the collected training data. Here, the artificial intelligence model uses a convolutional neural network mainly but is not limited thereto, and may include machine learning, deep learning, supervised learning, unsupervised learning, or the like.

The learning unit 120 learns a detection model, one or more individual analysis models, and an integrated analysis model.

A model used in the learning unit may be a deep neural network including one or more layers, and may be a convolutional neural network (CNN) including a plurality of convolution layers for creating a feature map including features of a region of interest and a pooling model for performing subsampling between the convolution layers. The convolutional neural network may extract an analysis result from the input image by alternately performing convolution and subsampling on the input image.

Specifically, in learning for detection, the learned detection model is generated by building training data in which regions to be automatically detected in an image are labeled, and learning an artificial intelligence detection model, which is developed to be optimized for detection of a specific region, with the training data.

In learning for analysis, the learned analysis model is generated by building training data in which classification criteria are applied for an image to be analyzed and regions within the image, and learning an artificial intelligence analysis model, which is developed to automate classification for a specific purpose, with the training data.

The detection model, one or more individual analysis models, and the integrated analysis model may be implemented as independent AI models, respectively, or may be linked to each other to be implemented as a single AI model. Accordingly, one or more artificial intelligence models corresponding to the above-described configurations may be implemented by one or more computing devices.

As shown in FIG. 3, an artificial intelligence model includes an automatic region detection model A that detects a region of interest in response to the collected medical image, an individual analysis model B that separately analyzes one or more regions of interest detected by the automatic region detection model A, and an integrated analysis model C that detect a severity of arthritis analyzed by integrating the analyzed results from the individual analysis model B.

As described above, the result value obtained from the automatic region detection model A may be used as an input value of the individual analysis model B, and the result value obtained from the individual analysis model B may be used as an input value of the integrated analysis model C.

In detail, the automatic region detection model A is a model that detects regions of interest which are a basis for determining the severity of arthritis in the collected medical image, and represents the automatic region detection model. For example, the automatic region detection model A may detect individual regions such as a joint region, which is a basis for determining reduction of a joint cavity gap, osteoproliferation probable region, which is a basis for determining presence or absence of osteoproliferation (osteophyte, bone protrusion) or a progressing degree of osteoproliferation, and a frequent region of subchondral bone hardness, which is a basis for determining hardness information of a subchondral bone, from one medical image.

The automatic region detection model A may be implemented as independent AI models that detect the regions of interest, respectively, or may be implemented as a single AI model to implement a plurality of AI models that detect the regions of interest for one medical image.

In this case, the automatic region detection model A may be linked to detect a region of interest corresponding to a region to be analyzed in the individual analysis model B. Accordingly, when the individual analysis model is added or changed, a function of automatically detecting an image of a region of interest that becomes an input image of a detection model may be included, or an artificial intelligence model for detecting the corresponding region of interest may be added.

The individual analysis model B includes an arthritis severity analysis model B-1, an osteoproliferation severity analysis model B-2, and a subchondral bone hardness severity analysis model B-n.

The arthritis severity analysis model B-1 may automatically detect features related to arthritis by analyzing a joint region. For example, the arthritis severity analysis model B-1 may detect features related to reduction of a joint cavity using an absolute value or a relative value for the reduction of the joint cavity.

The osteoproliferation severity analysis model B-2 performs an analysis on which grade features extracted from a corresponding osteoproliferation probable region correspond to, based on a preset grade classification of osteoproliferation. Therefore, the corresponding grade of the osteoproliferation can be detected.

The subchondral bone hardness severity analysis model B-n may detect a degree to which a subchondral bone part hardens from the frequent region of subchondral bone hardness and detect a corresponding grade based on a preset hardness severity grade classification of the subchondral bone.

The integrated analysis model C includes a degenerative arthritis severity analysis model C-1 and a degenerative arthritis progression prediction model C-2.

The degenerative arthritis severity analysis model C-1 may integrate result data analyzed in the arthritis severity analysis model B-1, the osteoproliferation severity analysis model B-2, and the subchondral bone hardness severity analysis model B-n, and calculate data that finely classifies a severity of degenerative arthritis from the collected medical image.

The degenerative arthritis progression prediction model C-2 may group and stratify the feature values detected in the individual analysis model B to perform learning step by step through the training data, so that not only the severity of arthritis but also prediction of future arthritis progression can be derived.

As such, the learning unit 120 may repeatedly learn each AI model based on the training data, and periodically re-learn each AI model based on a certain period or a specific criterion.

The detection unit 130 detects one or more regions of interest through the learned automatic region detection model A. Here, the region of interest refers to an image in which only a specific region of interest is detected from the collected medical image.

The detection unit 130 may pre-process the detected regions of interest based on an input format of the individual analysis model B corresponding to each region of interest. In other words, a size, resolution, or the like of the image corresponding to the region of interest may be changed according to the input format of the individual analysis model B.

The individual analysis unit 140 analyzes each region of interest to extract features related to the severity of arthritis, the severity of osteoproliferation, and the severity of subchondral bone hardness. In this case, the individual analysis unit 140 may acquire quantitative analysis data using the learned individual analysis model B.

In detail, the individual analysis unit 140 automatically extracts features from the region of interest through the learned arthritis severity analysis model.

The extracted features include reduction of a joint cavity and a degree of imbalance between medial and lateral sides in the reduction of the joint cavity, and further include features for diagnosing the arthritis.

In general, as the progressing degree of arthritis deepens, cartilage damage occurs and the joint cavity decreases. Further, in the degenerative arthritis, there is a characteristic that the reduction of the joint cavity occurs disproportionately centered on the medial or lateral side.

Accordingly, the individual analysis unit 140 extracts quantitative features of the joint cavity from the joint region through the learned arthritis severity analysis model.

For example, the individual analysis unit 140 may derive a length of the joint cavity in the joint region as an absolute value (mm, etc.) or as a relative value.

When deriving the numerical value JS of the joint cavity, the individual analysis unit 140 may extract a minimum medial value $JS_{min}^{M}$ of the joint cavity, an average medial value $JS_{avg}^{M}$ of the joint cavity for the medial side of the joint, or the like, and may extract a minimum lateral value $JS_{min}^{L}$ of the joint cavity, an average lateral value $JS_{avg}^{L}$ of the joint cavity, or the like for the lateral side of the joint.

Alternatively, the individual analysis unit 140 may derive the joint cavity gap as a relative value based on a width of a horizontal axis on the front in the joint region.

For example, the individual analysis unit 140 may calculate the joint cavity gap through "RJS (joint cavity gap)=JS (value of joint cavity)/W (width of knee joint)", thereby calculating the reduction of the joint cavity as an objectively-quantified numerical value regardless of the size of the region of interest, the size of the image, and the like.

The individual analysis unit 140 may calculate the severity of arthritis using a minimum value $Min\{RJS_{avg}^{L}, RJS_{avg}^{M}\}$ among the lateral and medial values of the joint cavity.

The severity of arthritis may be calculated based on a point at which the joint cavity gap is the minimum in the joint region, but it is not limited thereto. A user may set a criterion as an average value of the medial and lateral values of the joint cavity, and the criterion may be changed and designed.

Further, the individual analysis unit 140 may extract the degree of imbalance based on a difference between the reductions in the medial and lateral sides of the joint cavity based on the features of the degenerative arthritis.

The degree of imbalance between the medial and lateral sides of the joint cavity is calculated as in the following equation.

$$Ratio_{RJS} = \frac{Min\{RJS^L, RJS^M\}}{Max\{RJS^L, RJS^M\}}$$ Equation 1

As such, the individual analysis unit 140 derives an image feature according to the severity of arthritis in the knee joint region, a quantitative feature of the reduction of the joint cavity, and a feature of the degree of imbalance between the medial and lateral sides in the reduction of the joint cavity.

On the other hand, the individual analysis unit 140 automatically extracts features of osteoproliferation in an osteoproliferation probable region through the osteoproliferation severity analysis model.

The individual analysis unit 140 determines presence or absence of the osteoproliferation and estimates a degree of osteoproliferation. Further, the individual analysis unit 140 may derive which grade the estimated degree of osteoproliferation corresponds to, based on a preset grade classification of osteoproliferation.

Here, the grade classification of osteoproliferation may be modified by a change in a type of grade, a severity of osteoproliferation for each grade, or the like, and the osteoproliferation severity analysis model may be re-learned by using the modified grade classification of osteoproliferation.

Further, the individual analysis unit 140 automatically extracts features of subchondral bone hardness from a frequent region of subchondral bone hardness through the learned subchondral bone hardness severity analysis model.

The individual analysis unit 140 determines presence or absence of the subchondral bone hardness and estimates a progressing degree of subchondral bone hardness. In addition, the individual analysis unit 140 may derive which grade the estimated progressing degree of subchondral bone hardness corresponds to, based on a preset severity grade of subchondral bone hardness.

Here, the severity grade of subchondral bone hardness may be modified by a change in a type of grade, a severity of subchondral bone hardness for each grade, or the like, and the subchondral bone hardness severity analysis model may be re-learned by using the modified severity grade of subchondral bone hardness.

As such, the individual analysis unit 140 quantitatively extracts the features that are various conditions for estimating the severity of arthritis for each region of interest.

Although it is described that the individual analysis unit 140 extracts the severity of arthritis, the severity of osteoproliferation, and the severity of subchondral bone hardness, it is not limited thereto, and the individual analysis unit 140 may extract features for diagnosing the arthritis through the learned artificial intelligence model.

The integrated analysis unit 150 analyzes the severity of arthritis in the medical image by integrating the results analyzed by the individual analysis unit 140.

The integrated analysis unit 150 may collect features extracted for individual regions and finely classify the severity of degenerative arthritis derived from the respective features through a learned degenerative arthritis severity analysis model.

In detail, the integrated analysis unit 150 may convert the features extracted from the individual analysis unit 140 into vectors, respectively, and input the converted vectors to the learned degenerative arthritis severity analysis model to derive the severity of degenerative arthritis.

Further, the integrated analysis unit 150 may predict progression of arthritis in the future using the learned degenerative arthritis progression prediction model. At this time, if the integrated analysis unit 150 receives more information such as the severity of degenerative arthritis derived from the medical image at a previous time, the age, sex, or anything unusual of each patient, or the like, it is possible to accurately predict the progression of arthritis for each patient.

In addition, the control unit 160 may output the extracted feature values, the estimated grade of severity, the quantitative numerical value, and the like for the medical image of the individual analysis unit 140 or the integrated analysis unit 150

In this case, the control unit 160 may convert the extracted feature values, the estimated grade of severity, the quantitative numerical value, and the like into a table or graph and output the converted table or graph.

As such, the apparatus 100 may provide quantitative determination basis for each region with respect to the severity of arthritis derived by precisely analyzing the medical image.

Figure 4:
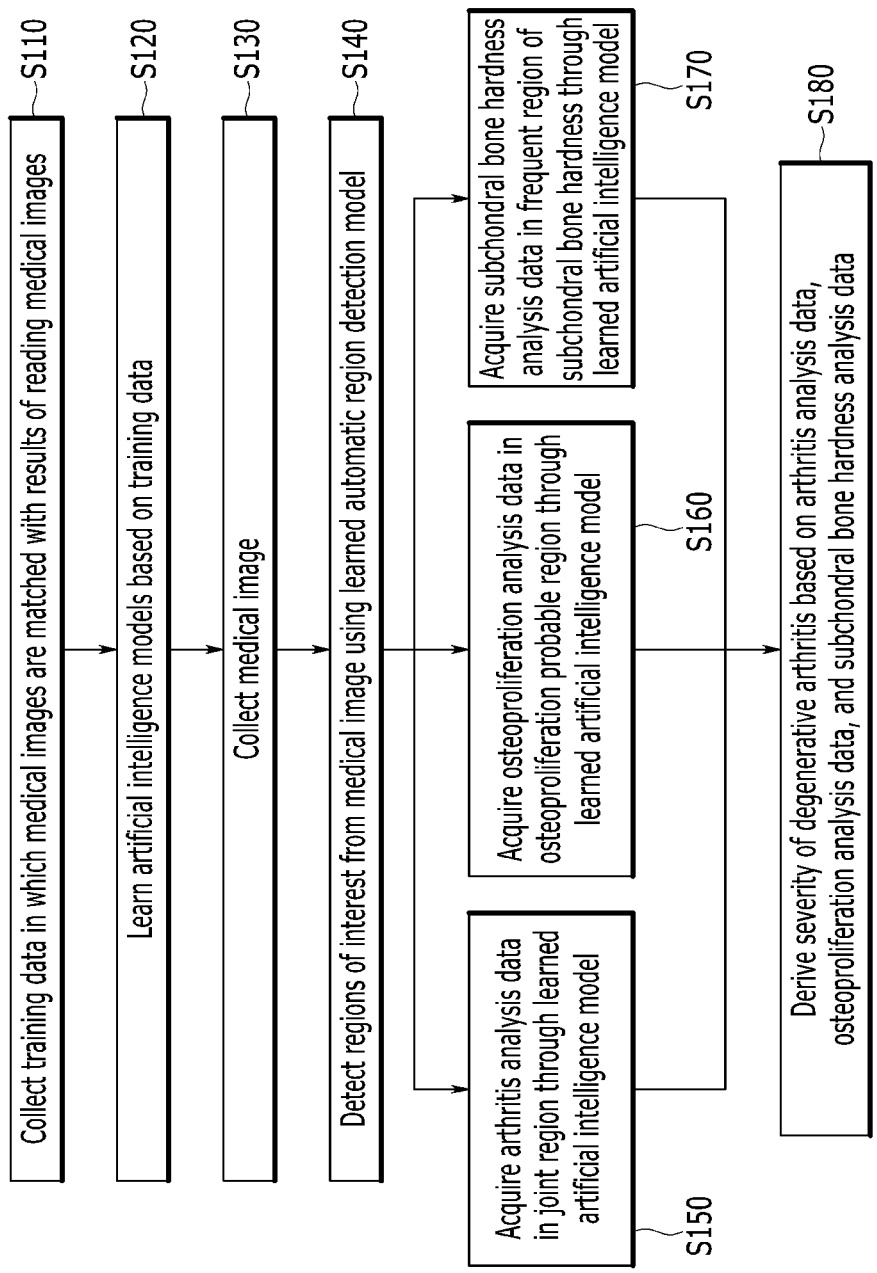
FIG. 4 is a flowchart showing a method for a precise analysis of a severity of arthritis according to an embodiment of the present invention.
Figure 5:
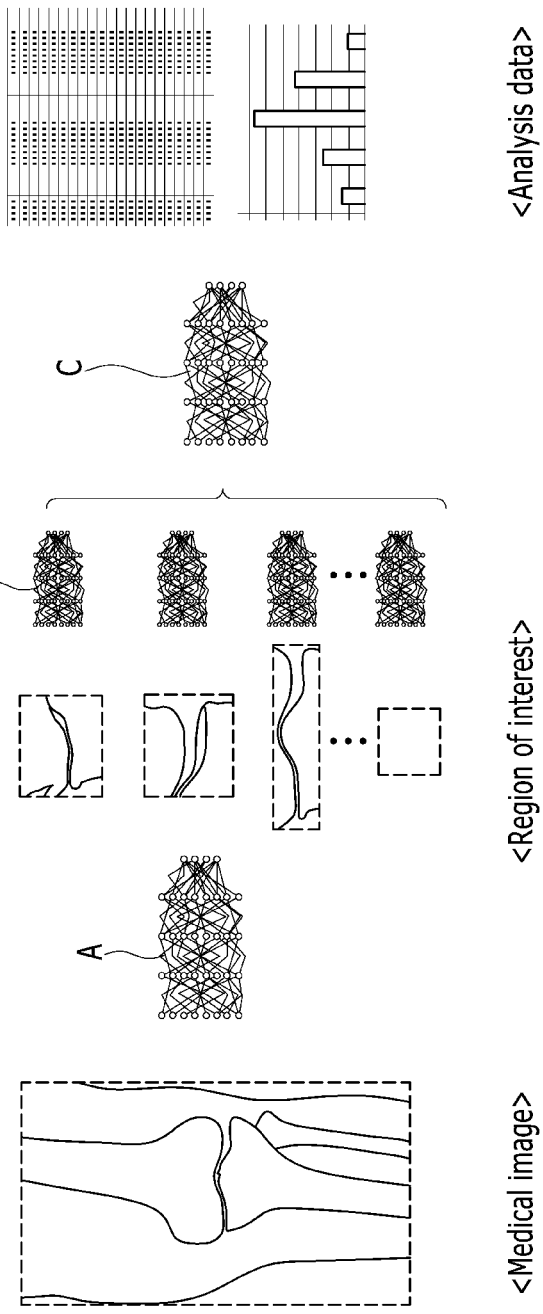
FIG. 5 is an example diagram showing an analysis image based on a medical image according to an embodiment of the present invention.

FIG. 4 is a flowchart showing a method for a precise analysis of a severity of arthritis according to an embodiment of the present invention, and FIG. 5 is an example diagram showing an analysis image based on a medical image according to an embodiment of the present invention.

As shown in FIG. 4 and FIG. 5, an apparatus 100 for a precise analysis of a severity of arthritis collects training data in which a plurality of medical images are matched with results of reading the corresponding medical images (S110).

The apparatus 100 may collect the training data through a database in which medical images captured at a previous time and data read by experts are stored, or build the training data with medical images generated according to a certain criterion through a certain simulation program.

For example, when using the simulation program, the apparatus 100 may set feature values based on various criterion values such as a KL grade classification criterion according to a severity grade of arthritis, a criterion for a grade classification of osteoproliferation, and a criterion for a severity grade classification of subchondral bone hardness, and build the training data by generating medical images according to the corresponding features values.

Next, the apparatus 100 learns a plurality of artificial intelligence models based on the collected training data (S120).

The apparatus 100 may learn an automatic region detection model that detects a region of interest from a medical image, an individual analysis model that detects reduction of a joint cavity, a degree of joint cavity imbalance, a severity of arthritis, a severity of osteoproliferation, and a severity of subchondral bone hardness based on one or more regions of interest, and an integrated analysis model that predicts progression of degenerative arthritis.

Here, the individual analysis model and the integrated analysis model may be implemented as a plurality of corresponding artificial intelligence models based on the detected feature values.

In addition, a plurality of regions of interest obtained from the automatic region detection model are used as input values of the individual analysis model, and feature values for each region obtained from the individual analysis model are used as an input value of the integrated analysis model.

In this case, when deriving the feature values for each region in the individual analysis model, one region of interest may be used as the input value or a plurality of regions of interest may be set as the input value.

The apparatus 100 iteratively learns each artificial intelligence model until the feature values for each region, the severity of degenerative arthritis, and the progression prediction of degenerative arthritis finally inferred from the training data match those read from the training data.

Further, the apparatus 100 builds the artificial intelligence model by setting weights of the learned artificial intelligence model.

Meanwhile, steps S110 and S120 may be performed only in a process of initially building the artificial intelligence model, and may be performed in a separate device.

Next, the apparatus 100 collects a medical image (S130).

The apparatus 100 may collect the medical image captured in real time from a connected medical image capturing device or collect the medical image from a connected database.

The apparatus 100 detects a plurality of regions of interest from the medical image using the learned automatic region detection model (S140).

The apparatus 100 may detect the regions of interest based on the learned individual analysis model. Upon detecting each of the regions of interest, the apparatus 100 may input each of the regions of interest to a corresponding individual analysis model according to the detection order of the regions of interest, or may input the regions of interest into individual analytical models at the same time.

In other words, steps S150 to S170 may be performed sequentially in a predetermined order or simultaneously.

The apparatus 100 acquires arthritis analysis data in a joint region through the learned artificial intelligence model (S150).

The apparatus 100 acquires the arthritis analysis data indicating a severity of arthritis, a quantitative feature value for reduction of a joint cavity, an imbalance degree of reduction of the joint space, and the like in a joint region. In this case, each of the acquired arthritis analysis data includes a quantitative value.

The apparatus 100 acquires osteoproliferation analysis data in an osteoproliferation probable region through the learned artificial intelligence model (S160).

The apparatus 100 acquires the osteoproliferation analysis data indicating feature values representing presence or absence of osteoproliferation and a degree of osteoproliferation, a grade of osteoproliferation, and the like.

The arthritic severity precision analysis apparatus 100 acquires subchondral bone hardness analysis data in a frequent region of subchondral bone hardness through the learned artificial intelligence model (S170).

The apparatus 100 acquires the subchondral bone hardness analysis data indicating a feature value representing a degree of subchondral bone hardness, a severity grade of subchondral bone hardness, and the like.

The arthritic severity precision analysis apparatus 100 may store the analysis data obtained in steps S150 to S170 in a separate database, and may output the analysis data to a display unit or a connected terminal.

Next, the apparatus 100 derives a severity of degenerative arthritis based on the arthritis analysis data, the osteoproliferation analysis data, and the subchondral bone hardness analysis data (S180).

The apparatus 100 may convert the analysis data into vectors, respectively, and apply them as input values of an artificial intelligence model (a degenerative arthritis severity detection model and a degenerative arthritis progression prediction model). In this case, the apparatus 100 may combine the numerical values of each analysis data and codes for items that the numerical values mean to generate the vector.

Further, the apparatus 100 may finely classify the severity of degenerative arthritis by analyzing a correlation between each feature of the analysis data and the analysis data through the learned degenerative arthritis severity analysis model.

Furthermore, the apparatus 100 may predict the progression of arthritis in future based on the correlation between each feature of the analysis data and the analysis data and the finely classified severity of degenerative arthritis through the learned degenerative arthritis progression prediction model.

The apparatus 100 may store the severity of degenerative arthritis and the progression prediction data of the arthritis analyzed and obtained as described above in a separate database, and may convert them into a table or graph and output to the table or graph a display unit or a connected terminal.

Figure 6:
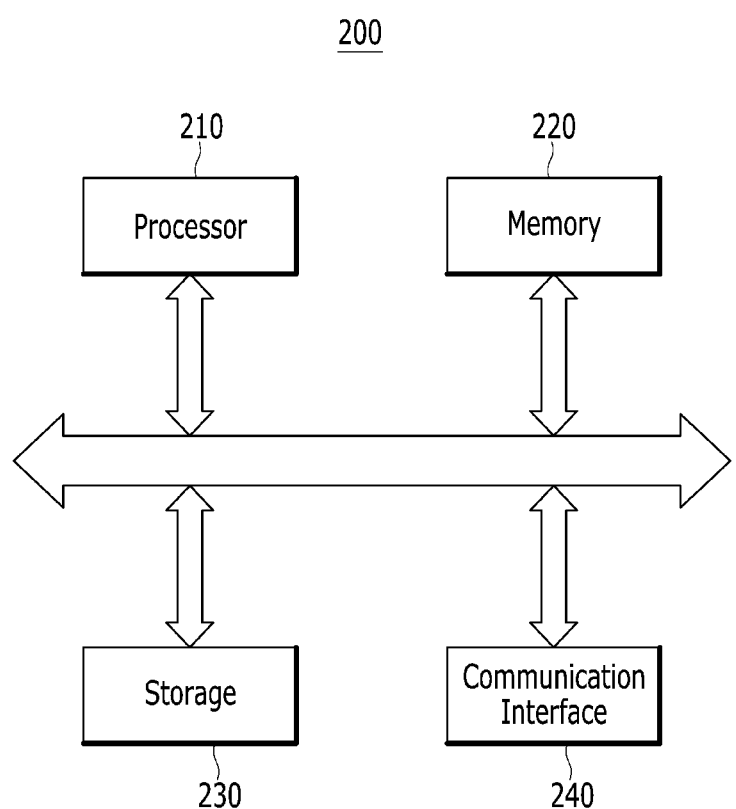
FIG. 6 is a hardware configuration diagram of a computing device according to an embodiment of the present invention.

FIG. 6 is a hardware configuration diagram of a computing device according to an embodiment of the present invention.

As shown in FIG. 6, hardware of the computing device 200 may include one or more processors 210, a memory 220, a storage 230, and a communication interface 240 that may be connected through a bus. In addition, hardware such as an input device and an output device may be included. Various software including an operating system capable of running a program may be loaded in the computing device.

The processor 210 is a device for controlling an operation of the computing device 200, and may be a processor 210 of various types for processing instructions included in a program. The processor may be, for example, a central processing unit (CPU), a microprocessor unit (MPU), a micro controller unit (MCU), a graphic processing unit (GPU), or the like. The memory 520 loads a corresponding program so that the instructions described to execute operations of the present invention are processed by the processor 210. The memory 220 may be, for example, read only memory (ROM), random access memory (RAM), or the like. The storage 230 stores various data and programs required for executing the operations of the present invention. The communication interface 240 may be a wired/wireless communication module.

As described above, it is possible to more precisely classify the severity of arthritis, by calculating the severity of arthritis based on individual analysis data analyzed for each region of interest through main regions of interest in the medical image.

Further, a reliability of the result data of the classified severity of arthritis can be secured by providing the individual analysis data that serves as a medical basis for classifying the severity of arthritis.

Furthermore, it is possible to provide not only the severity of arthritis but also the prediction data of the progression of arthritis in future, based on the feature values extracted through the artificial intelligence model.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims.

The invention claimed is:

1. An apparatus for a precise analysis of a severity of arthritis, comprising:
   an image collection unit configured to collect a medical image having captured a joint of a user,
   a region detection unit configured to detect one or more regions of interest for analyzing arthritis in the medical image through a learned automatic region detection model,
   an individual analysis unit configured to extract quantitative feature values from the detected regions of interest, and derive one or more individual analysis data from among a severity of arthritis, a severity of osteoproliferation, and a severity of subchondral bone hardness based on the feature values; and
   an integrated analysis unit configured to finely classify a severity of degenerative arthritis through an integrated analysis model learned based on the individual analysis data,
   wherein the one or more regions of interest comprise at least one of a joint cavity region, an osteoproliferation probable region, or a subchondral bone region, and
   wherein the quantitative feature values comprise at least one of a first quantitative feature value for estimating reduction of a joint cavity extracted from the joint cavity region, a second quantitative feature value for presence or absence of osteoproliferation or a progressing degree of osteoproliferation, extracted from the osteoproliferation probable region, or a third quantitative feature value for a progressing degree of subchondral bone hardness, extracted from the subchondral bone region.

2. The apparatus of claim 1, further comprising a learning unit configured to:
   detect regions of interest from a training medical image based on training data in which training medical images having captured a joint are matched with result data of reading the training medical images; and
   learn an individual analysis model configured to analyze a correlation between feature values extracted from the detected regions of interest and the result data.

3. An apparatus for a precise analysis of a severity of arthritis, comprising:
   an image collection unit configured to collect a medical image having captured a joint of a user;

a region detection unit configured to detect one or more regions of interest for analyzing arthritis in the medical image through a learned automatic region detection model;

an individual analysis unit configured to extract quantitative feature values from the detected regions of interest, and derive one or more individual analysis data from among a severity of arthritis, a severity of osteoproliferation, and a severity of subchondral bone hardness based on the feature values;

an integrated analysis unit configured to finely classify a severity of degenerative arthritis through an integrated analysis model learned based on the individual analysis data; and a learning unit configured to:
detect regions of interest from a training medical image based on training data in which training medical images having captured a joint are matched with result data of reading the training medical images; and learn an individual analysis model configured to analyze a correlation between feature values extracted from the detected regions of interest and the result data, wherein the individual analysis model comprises:
an arthritis severity analysis model configured to extract quantitative feature values for estimating reduction of a joint cavity based on a region of interest in which a joint cavity region is detected;

an osteoproliferation severity analysis model configured to extract quantitative feature values for presence or absence of osteoproliferation or a progressing degree of osteoproliferation based on a region of interest in which an osteoproliferation probable region is detected; and a subchondral bone hardness severity analysis model configured to extract quantitative feature values for a progressing degree of subchondral bone hardness based on a region of interest in which a subchondral bone region is detected.

4. The apparatus of claim 3, wherein the individual analysis unit is configured to:
estimate a medial value of the joint cavity and a lateral value of the joint cavity in the region of interest through the arthritis severity analysis model to extract a quantitative value of a severity of arthritis by an average of the medial value and the lateral value; and
calculate a ratio of imbalance between the medial value and the lateral value.

5. The apparatus of claim 3, wherein the individual analysis unit is configured to:
detect osteophyte or bone protrusion indicating the osteoproliferation in the region of interest through the osteoproliferation severity analysis model and extract a corresponding osteoproliferation grade from among preset osteoproliferation grades; and
detect a degree of subchondral bone hardness in the region of interest through the subchondral bone hardness severity analysis model and extract a corresponding hardness severity grade from among preset hardness severity grades of subchondral bone.

6. The apparatus of claim 3, wherein the learning unit is configured to:
convert the individual analysis data obtained from the individual analysis model based on the training data into vectors, respectively; and learn the integrated analysis model configured to analyze a correlation between the vectors using the vectors, and
wherein the integrated analysis model comprises:
a degenerative arthritis severity analysis model configured to finely classify a severity for progressing degree of degenerative arthritis based on the individual analysis data; and
a degenerative arthritis progression prediction model configured to predict progression of degenerative arthritis based on the individual analysis data and the severity of degenerative arthritis.

7. The apparatus of claim 6, wherein the integrated analysis unit is configured to:
integrate the individual analysis data through the degenerative arthritis severity analysis model to precisely analyze the severity of degenerative arthritis in the medical image; and
predict the progression of degenerative arthritis in future through the degenerative arthritis progression prediction model.

8. The apparatus of claim 7, further comprising a control unit configured to output one or more feature values from among feature values corresponding to one or more individual analysis data derived from the individual analysis unit and features values for the severity of degenerative arthritis derived from the integrated analysis unit.

9. A program configured to be stored in a non-transitory computer-readable storage medium and to be executed by a processor, the program comprising instructions to execute:
detecting, based on a collected medical image, one or more regions of interest for analyzing arthritis in the medical image through an automatic region detection model;
extracting quantitative feature values from the detected regions of interest, and deriving one or more individual analysis data from among a severity of arthritis, a severity of osteoproliferation, and a severity of subchondral bone hardness based on the feature values, through an individual analysis model;
finely classifying a severity of degenerative arthritis analyzed based on the individual analysis data, through an integrated analysis model; and
outputting the classified severity of degenerative arthritis and the individual analysis data to a connected terminal,
wherein the automatic region detection model is a model that has been learned to detect a region of interest for estimating result data from a training medical image based on training data in which training medical images are matched with result data of reading the training medical images;
wherein the individual analysis model is a model that has been learned configured to extract feature values from the detected region of interest and analyze a correlation between individual analysis data of the feature values and the result data; and
wherein the integrated analysis model is a model that has been learned to analyze a correlation between data in which the feature values acquired from the individual analysis model are integratively analyzed and the result data.

10. The program of claim 9, wherein the region of interest comprises one or more among a joint cavity region, an osteoproliferation probable region, and a subchondral bone region, and
wherein deriving the one or more individual analysis data comprises estimating a medial value of the joint cavity and a lateral value of the joint cavity in the region of interest in which the joint cavity region through an arthritis severity analysis model to calculate a quantitative value of a severity of arthritis by an average of the medial value and the lateral value, and a ratio of imbalance between the medial value and the lateral value of the joint cavity.

11. The program of claim 9, wherein finely classifying the severity of degenerative arthritis comprises:
  integrating the individual analysis data through an integrate analysis model to finely analyze the severity of degenerative arthritis in the medical image; and
  predicting progression of degenerative arthritis based on the individual analysis data and the severity of degenerative arthritis.

* * * * *